(12) United States Patent
Kohlmüller

(10) Patent No.: US 7,180,294 B2
(45) Date of Patent: Feb. 20, 2007

(54) METHOD FOR PLANNING AND PERFORMING A MAGNETIC RESONANCE EXAMINATION, MAGNETIC RESONANCE APPLIANCE AND COIL UNIT

(76) Inventor: Rüdiger Kohlmüller, Ohmstr. 5, 91058 Erlangen (DE)

( * ) Notice: Subject to any disclaimer, the term of this patent is extended or adjusted under 35 U.S.C. 154(b) by 0 days.

(21) Appl. No.: 11/333,611

(22) Filed: Jan. 17, 2006

(65) Prior Publication Data
US 2006/0164086 A1   Jul. 27, 2006

(30) Foreign Application Priority Data
Jan. 21, 2005   (DE) .................. 10 2005 002 982
Dec. 21, 2005   (DE) .................. 10 2005 061 209

(51) Int. Cl.
*G10V 3/00*   (2006.01)

(52) U.S. Cl. ...................... 324/318; 600/421

(58) Field of Classification Search ................ 324/318, 324/322; 600/421, 422
See application file for complete search history.

(56) References Cited

U.S. PATENT DOCUMENTS

| | | | |
|---|---|---|---|
| 4,973,907 A | 11/1990 | Bergman et al. | |
| 5,066,915 A | 11/1991 | Omori et al. | |
| 5,551,430 A * | 9/1996 | Blakeley et al. | ............ 600/410 |
| 6,529,762 B1 | 3/2003 | Ladebeck | |
| 6,759,846 B2 * | 7/2004 | Van Helvoort et al. | ..... 324/300 |

FOREIGN PATENT DOCUMENTS

| | | |
|---|---|---|
| DE | 40 20 477 A1 | 1/1991 |
| DE | 195 08 715 A1 | 9/1996 |
| DE | 199 43 404 A1 | 4/2001 |
| EP | 0 374 994 A1 | 6/1990 |

* cited by examiner

*Primary Examiner*—Louis M. Arana

(57) ABSTRACT

The invention relates to a method for planning and performing a magnetic resonance examination using a magnetic resonance appliance, in which at least one coil unit is arranged on the patient and at least two areas are examined. The coil unit comprises an input panel and possibly an optical coil-specific marker. In the method taking place automatically, activation operations on at least one input panel cause the coil unit(s) and hence the areas of the patient which are to be examined to be moved into the magnetic resonance appliance's isocenter, for example. The advantage of this is that patient positioning is significantly simplified and speeded up and that the input panel can be used to carry out part of the measurement protocol creation on the patient in situ.

20 Claims, 2 Drawing Sheets

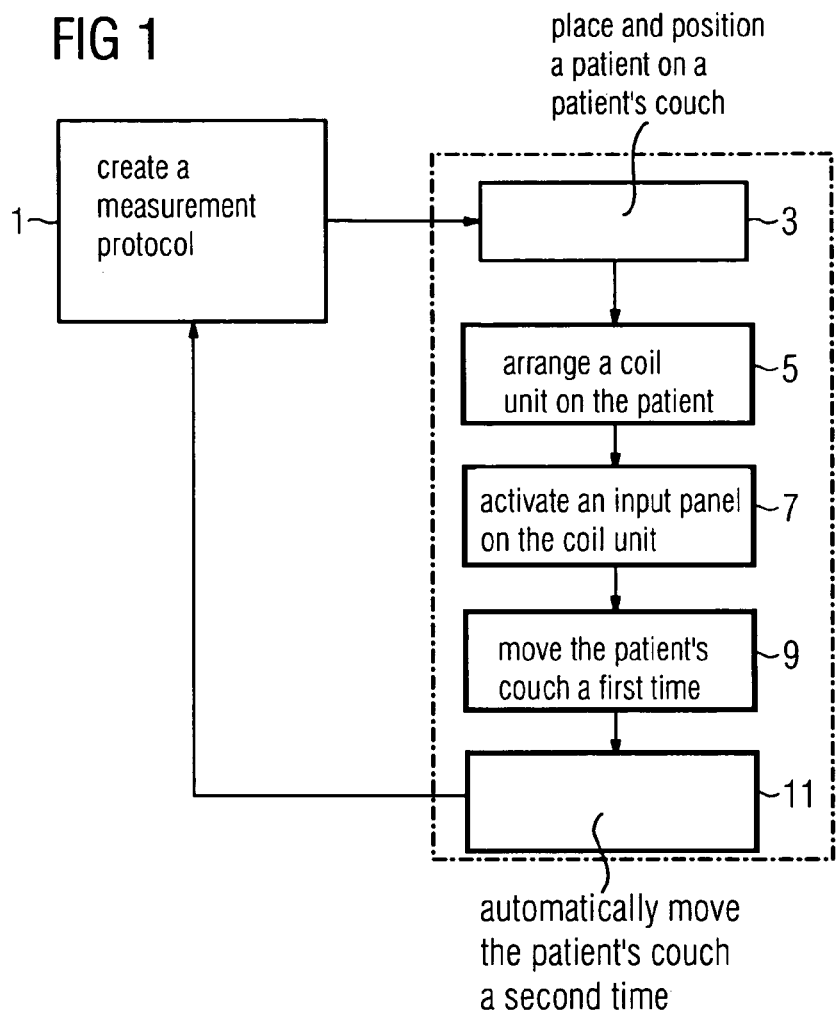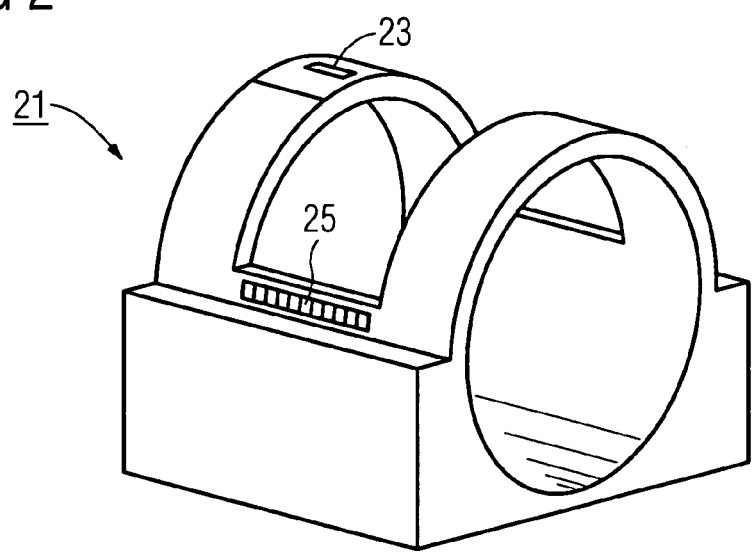

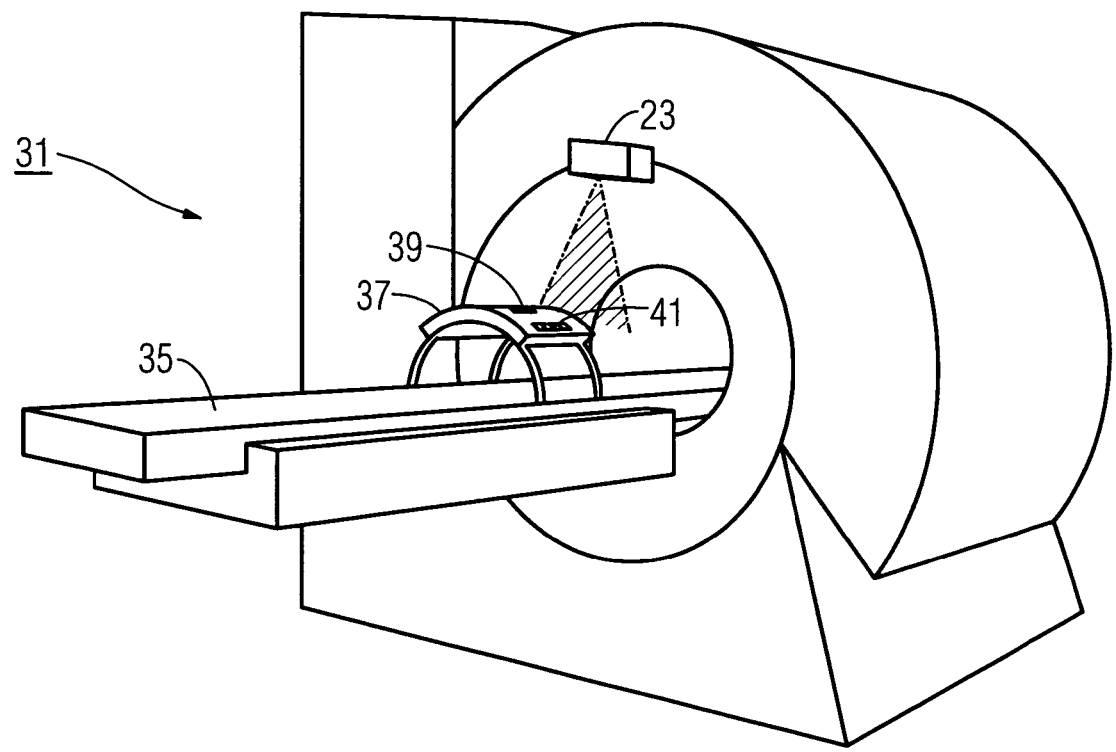

METHOD FOR PLANNING AND PERFORMING A MAGNETIC RESONANCE EXAMINATION, MAGNETIC RESONANCE APPLIANCE AND COIL UNIT

CROSS REFERENCE TO RELATED APPLICATIONS

This application claims priority to the German Applications No. DE 10 2005 002 982.5, filed Jan. 21, 2005 and DE 10 2005 061 209.1, filed Dec. 21, 2005 which are incorporated by reference herein in their entirety.

FIELD OF INVENTION

The invention relates to a method for planning and performing a magnetic resonance examination on a patient and to a magnetic resonance appliance having a patient's couch and having at least one coil unit and to a coil unit for such a magnetic resonance appliance.

BACKGROUND OF INVENTION

A magnetic resonance examination (MR examination) involves an area which is to be depicted from an examination object, for example the head of a patient, being positioned in an examination area of the magnetic resonance appliance for the purpose of imaging. For optimum image quality, the area to be depicted is preferably put into an area of the examination area whose basic magnetic field from a basic field magnet in the magnetic resonance appliance is as constant as possible. That is to say that attempts are made to arrange the area to be depicted close to the "isocenter" of the examination area.

SUMMARY OF INVENTION

Normally, the patient is positioned in the examination area's isocenter manually using a laser system which is arranged in the area of the aperture of the basic field magnet. When the object to be examined (e.g. the patient or an MR phantom) has been positioned on the patient's couch with the coils or coil units required for examination, an operator (e.g. a radiologist or service engineer) moves the object under the laser system, which is generally situated above the aperture. The laser system projects a cross-like coordinate system (laser cross) onto the object which is to be examined. The operator now needs to move the laser cross onto a marker on one of the coils or to another desired position by manually moving the couch to and fro. Next, a further push of a button moves the patient's couch into the basic field magnet, with the selected location being moved into the isocenter. The distance to be moved between the position of the laser cross and the isocenter is measured when the magnetic resonance appliance is commissioned.

DE 40 20 477 A1 discloses an RF coil positioning apparatus for an MR appliance, in which the passage of an RF coil unit is detected by a coil detector and the RF coil unit is positioned in the center of the magnetostatic field using a control circuit to actuate the patient's couch position.

In addition, DE 195 08 715 A1 discloses an apparatus in which a marker fixed on the patient is detected from whose physical location a movement distance is determined and the patient's couch is accordingly moved.

EP 0 374 994 A1 discloses an RF coil system in which coil-specific markers are used to identify the coils used in an MR image.

DE 199 43 404 A1 discloses the use of specific diagnostic questioning for automatically stipulating measurement parameters for subsequent MR measurements.

It is an object of the invention to replace repeated manual intervention in patient positioning in the case of several successive magnetic resonance examinations with an automatable method for patient positioning in order to simplify the planning and performance of MR examinations.

The object is achieved by the claims.

The inventive method for planning and performing a magnetic resonance examination on a patient using a magnetic resonance appliance permits the examination of at least one first and a second area of the patient which require a first and a second insertion path for the patient in the magnetic resonance appliance. As usual, examination involves a measurement protocol being called which is designed to examine the areas using a plurality of coil units and/or a plurality of coils in one or more coil units. As usual, this involves the patient to be examined being positioned on a patient's couch on the magnetic resonance appliance, and at least one coil unit is arranged on the patient. In the case of one coil unit, the two areas may need to be examined just in various positions relative to the coil unit. However, the coil unit may also have a plurality of coils, among which respective different combinations of coils are used for the various areas. Activating at least one first input panel on the at least one coil unit makes an input into the measurement protocol regarding the second insertion path for the patient. The patient's couch is moved in accordance with the first insertion path and the first magnetic resonance examination is performed. With regard to the first movement, the movement is free to the ex tent that in this case it is possible to use an ordinary manual procedure, or else one which is similar to the second movement. However, activation allows subsequent examinations to be automated. The second automatic movement of the patient's couch is effected on the basis of the input in the measurement protocol, so that the second magnetic resonance examination in the second area can be performed.

In the method based on the invention, a plurality of coil units and/or a plurality of coils in one or more coil units are used to plan or perform MR examinations. In this case, at least one coil unit has one or more input panels which allow the operator to transmit additional information to a measurement protocol, underlying the MR examination, for the magnetic resonance appliance. The input panel is used to notify the measurement protocol/magnetic resonance appliance of which coil needs to be positioned in the isocenter, for example. Using an expanded input panel, it is possible to make a very differentiated position selection. Thus, the operator can select an appropriate input panel on the input panel to decide which one-dimensional, two-dimensional or three-dimensional position and/or which coil is moved into the isocenter of the basic magnetic field. To this end, by way of example, an input panel may have the associated use of a specific coil/coil combination in the coil unit or an associated particular additional path of movement. In addition, the timing order for operating input panels, e.g. including input panels on different coil units, or the arrangement of the latter in the direction of movement can have an influence on the order for measurement with the various coil units or with various coils in a coil unit.

Hence, in one preferred embodiment of the method, the examination position is set by activating an input panel fitted on the coil unit, particularly a sensor control panel, pressure panel or keypad.

The method for planning and performing a magnetic resonance examination on a patient in accordance with the invention involves a measurement protocol, which contains the parameters of the RF pulse sequences which are to be used for the purpose of generating magnetic resonance signals, for example, additionally incorporating the position of the coil unit which is identified by the detector system and/or additional information on the basis of the activation of input panels. As a result—following the arrangement of the coil units and the activation of the input panels and hence, by way of example, the stipulation of the order of the areas to be depicted which are to be approached—it is possible to start the measurement, and the magnetic resonance appliance uses various coils or coil units on the various areas to be depicted in order to perform the magnetic resonance examinations. Manual intervention of the operator in the meantime is not required in this case.

One advantage of the invention is the time saving for the user of the magnetic resonance appliance. Complex manual positioning (manually turn on the laser, move the table to and fro to an exact position, turn off the laser, initiate movement of the table into the magnet) is dispensed with. The examining radiologist therefore obtains a time saving, and it can increase the patient throughput.

Another advantage is the simplification of precautionary examinations on the entire body, i.e. in the case of screening examinations on various regions of the body of a patient. In the case of such examinations, exact orientation of the layers which are to be measured is not required for the time being.

Another crucial advantage is the reduction in exposure of the operating personnel and of the patient to the strong static magnetic field from the magnetic resonance appliance, since the invention shortens the time to remain in the scatter field from the basic field magnet. This allows a user to work on the magnetic resonance appliance for a longer time. In addition, the complex laser positioning system and the costs associated therewith are dispensed with.

In one advantageous embodiment, the method is performed using a magnetic resonance appliance which has at least one coil unit, the coil unit having an optically detectable coil-specific marker. In addition, the magnetic resonance appliance has an optical detector system for identifying this marker. It may be that such a coil unit can be attached only to a fixed location on the patient's couch, which means that the coil-specific marker must make only the coil unit itself identifiable, since the location of a receiving profile for the coil relative to the patient's couch is known only from the coil type. The marker and the optical detector system represent an automatic position identification system, as can be formed by a video camera with image processing to identify the coil-specific marker, for example.

In line with the method, the patient is positioned on a patient's couch on the magnetic resonance appliance, and at least one coil unit is arranged on the patient in the area of one or more areas which are to be depicted. The patient's couch is then moved such that the detector system can identify the position of the coil unit from the marker. The identification of the coil unit(s) likewise allows automated movement of the patient's couch along a path of movement which puts the coil unit into an examination position for the magnetic resonance examination.

The path of movement is obtained firstly from the position of the marker, this being able to be prescribed by the detector system or its physical arrangement, for example, and secondly from the design of the coil unit or the position of the marker on the coil unit. The reason is that a substep in an MR examination is moving the area to be depicted into a desired area, e.g. into the isocenter of the basic magnetic field. When the receiving profile for the coil unit has been stipulated, for example, and when said receiving profile has its center situated under the marker, the path of movement corresponds to the distance between the isocenter of the basic field magnet and the position of the marker during identification by the detector system, for example. In the case of flexibly usable coil units, in which a wide variety of three-dimensional areas can be detected in targeted fashion by combining various coils in the coil unit, for example, the path of movement is additionally dependent on the location of the coils to be used relative to the marker. In this case, the path of movement can be determined as appropriate if the coils to be used and their position relative to the marker are known.

Further advantageous embodiments of the invention are characterized by the features of the dependent claims.

BRIEF DESCRIPTION OF THE DRAWINGS

The text below explains a plurality of exemplary embodiments of the invention with reference to FIGS. 1 to 3, in which FIG. 1 shows a flowchart to clarify the methods, FIG. 2 shows a schematic illustration of a head coil having a sensor panel and a marker, and FIG. 3 shows a schematic illustration of the integration of the fundamental components for the method into an MR appliance.

DETAILED DESCRIPTION OF INVENTION

To plan and perform an MR examination using an MR appliance, a user creates a measurement protocol 1. This defines the MR examination, i.e. the parameters to be chosen regarding radio-frequency excitation, reception of the magnetic resonance signals, the coils used, the orientation of the layers, the number of layers etc. are selected. Recording an area which is to be depicted requires that this area be positioned in the homogeneous central area of the basic magnetic field from the MR appliance. At the same time as or following the creation of the measurement protocol in its broad outline, the patient is placed and positioned 3 on a patient's couch on the MR appliance. In line with the areas which are to be depicted, at least one coil unit is arranged 5 on the patient. This also involves activating 7 at least one input panel on the coil unit(s). As a result of the activation 7, the MR appliance receives information, for example, about which coil needs to be used or whether there needs to be a slight offset in the positioning relative to the isocenter, for example, as regards the receiving profile for the coil unit. Possibly, a first area to be examined is also moved to the target cross of a laser system at the entry to the MR appliance. This concludes the planning of the MR examination on the patient himself, and the operating personnel can leave the room. In the next step, the patient's couch is moved a first time 9, which involves a first area of the patient being positioned in the isocenter.

Generally, while the patient's couch is being moved, a marker on a coil unit can be identified optically, for example, by a detector system and used, by way of example, to determine a path of movement With coil data stored in the MR appliance with or without information on the basis of the activation 7. To this end, the patient as a whole, for example, can be moved through once under the detector system in order to detect all the coils. Alternatively, when the patient is inserted into the basic magnet "in steps", paths of movement can be determined and stored on the basis of the respective detected coil unit.

In interaction with further parameters of the measurement protocol, the MR examination involves the patient's couch being automatically moved a second time 11, so that a second area of the patient is positioned in line with the activation 7, and the respective coil unit adopts the desired examination position for the MR examination in the MR appliance.

In this way, it is possible to perform any number of MR examinations in which the correct positioning of the patient/ of the coils (coil units) is still effected manually, possibly at the beginning, but at least automatically for subsequently pending MR examinations; assisted by the input panels on the coil units and possibly with the addition of the coil-specific information about the coil unit itself which (information) can be added using the markers.

FIG. 2 shows a head coil 21 having an optical coil-specific marker 23 and an input panel 25. The head coil unit 21 has a plurality of coils integrated in it which thus allow flexible imaging at various locations/body areas. The marker 23 is fitted on the top of the head coil unit 21 and allows it to be identified using optical identification methods. By way of example, it comprises a coded signature for the head coil unit 21 and a cross for accurate position-finding by a detector system. The head coil unit 21 is mounted permanently, for example, on a patient's couch, so that a data line—which can also run within the patient's couch, for example—can be used to transmit an appropriate signal to a control unit on a magnetic resonance appliance when one of the input panels 25 is activated. For a firmly associated position of the coil unit, it may not be necessary to use the marker. The required information about the coil unit is provided by the arrangement and fixing of the coil, for example. A central input panel, for example in the form of a pressure control panel, effects isocentric positioning of the head coil unit 21, i.e. the receiving profile for the head coil unit is overlaid centrally with the isocenter of the basic magnetic field from the MR appliance used. Arranged next to the central pressure panel are off-isocenter pressure panels which allow off-isocenter positioning. In this case, by way of example, each pressure panel corresponds to a movement by one millimeter, for example. In the case of patient's couches which can also be moved at right angles to the cylinder axis of the basic field magnet, the off-center positioning can also be achieved in two or three directions using appropriate input panels. In the technical implementation of the input panel, there is no restriction within the framework of the strong magnetic and RF fields, which means that, by way of example, pressure sensor panels, control panels etc. can be used which are activated by finger pressure or switching, for example.

When one or more input panels have been selected by the user, the magnetic resonance appliance begins to move the patient's couch into the magnet aperture, for example automatically. Using the optical identification system instead of the laser system, it is possible to detect the marker as it moves past and to evaluate it, together with the activation of the input panel, such that the patient's couch moves into the magnet to the extent that the marked position comes to rest in the isocenter.

The distance (or the travel time) which the patient's couch needs to cover in order to bring the object into the desired position can be ascertained by means of an alignment step, which is usual when the magnetic resonance installation is commissioned. This value is stored in a piece of system software. The system can use the alignment values to calculate what distance or what travel time for the table is required in order to move the detected position into the isocenter.

The method described in FIG. 1 can be used to assist the planning and performance of MR examinations. By preselecting various coils/coil units in different orders (e.g. a position is first selected on the head coil and then on a body coil), the examination of a patient in situ on the patient's couch is automatically transferred to a measurement protocol as planned and the examination is performed fully automatically. To this end, the examination planned by the user for the appropriate body region (e.g. which RF sequence type etc.) needs to be coupled to the selected coils/object position by means of software. Using the detection system and the software, it is possible to move the correct positions into the center and to start the MR examination in the software or controller. Once the first examination has concluded, e.g. the examination of the head, the next area to be depicted is automatically moved into the isocenter for the next MR examination, and the examination there is performed.

FIG. 3 shows an overall design for a magnetic resonance appliance 31 having an optical detector system 33, e.g. a video camera, a patient's couch 35 and a body coil 37, permanently mounted on the patient's couch 35 with a detectable marker 39 and an input panel 41. If the body coil 37 has a plurality of coils over a relatively large area then a plurality of input panels 41 can allow targeted actuation of various coils or receiving profiles. If a plurality of coil units are attached to the patient, for example additionally a head coil 21 in line with FIG. 2, then an order for using the coils can be stipulated for the various coil units using the input panels, in order to perform the MR examinations as a joint procedure.

The invention claimed is:

1. A method for planning and performing a magnetic resonance examination on a patient using a magnetic resonance device, wherein at least first and second areas of the patient are examined requiring first and second introduction paths for the patient to be inserted into the magnetic resonance device, the method comprising:
   accessing a measurement protocol configured to execute the magnetic resonance examination of the first and second areas using a plurality of coil units or a plurality of coils of at least one coil unit;
   positioning the patient on a patient couch of the magnetic resonance device;
   arranging at least one of the coil units on the patient;
   activating at least a first input panel of the at least one coil unit, the first input panel configured to trigger a first input into the measurement protocol regarding the second introduction path;
   performing a first movement of the patient couch according to the first introduction path;
   executing a first magnetic resonance examination relative to the first area;
   automatically performing a second movement of the patient couch based upon the first input; and
   executing a second magnetic resonance examination relative to the second area.

2. The method as claimed in claim 1, wherein wherein the first movement is performed manually using a laser system.

3. The method as claimed in claim 1, further comprising activating a second input panel of the at least one coil unit or of a coil unit different from the of the at least one coil unit, the second input panel configured to trigger a second input into the measurement protocol regarding the first introduction path, wherein the first movement is performed automatically based upon the second input.

4. The method as claimed in claim 1, wherein the at least one coil unit includes a detectable coil-specific marker, and the magnetic resonance device includes a detector for identifying the marker, the marker having information at least about a type of the at least coil unit, the method further comprising detecting the information by the detector when the marker is moved past the detector, wherein the first movement is performed automatically using the detected information.

5. The method as claimed in claim 4, wherein detecting the information includes detecting a position of the marker, the method further comprising defining the first introduction path based upon the detected information and the detected position such that a required position of a receiving profile of the at least one coil unit relative to the marker is achieved, the required position of the receiving profile related to the first magnetic resonance examination.

6. The method as claimed in claim 4, wherein the at least one coil unit is fixed to the patient couch, and the first introduction path is determined from the information about the type of the at least coil unit.

7. The method as claimed in claim 1, wherein the first input panel is a sensor control panel, a pressure panel or a keypad.

8. The method as claimed in claim 3, wherein the second input panel is a sensor control panel, a pressure panel or a keypad.

9. The method as claimed in claim 1, wherein activating the first input panel includes actuating a primary input panel of the first input panel, the primary input panel of the first input panel defining an examining position such that a receiving profile of the at least one coil unit surrounds an isocenter of the first or second examination area essentially symmetrically.

10. The method as claimed in claim 3, wherein activating the second input panel includes actuating a primary input panel of the second input panel, the primary input panel of the second input panel defining an examining position such that a receiving profile of the at least one coil unit surrounds an isocenter of the first or second examination area essentially symmetrically.

11. The method as claimed in claim 1, wherein activating the first input panel includes actuating a secondary input panel of the first input panel, the secondary input panel of the first input panel defining an examining position such that a receiving profile of the at least one coil unit asymmetrically surrounds an isocenter of the first or second examination area.

12. The method as claimed in claim 3, wherein activating the second input panel includes actuating a secondary input panel of the second input panel, the secondary input panel of the second input panel defining an examining position such that a receiving profile of the at least one coil unit asymmetrically surrounds an isocenter of the first or second examination area.

13. The method as claimed in claim 3, wherein the first and second magnetic resonance examinations are executed in a sequence according to such sequence in which the first and second input panels have been activated.

14. A magnetic resonance device, comprising:
a patient couch for accommodating a patient;
least one coil unit;
a control unit; and
a first input panel arranged on the coil unit, the first input panel configured to transmit upon activation a signal regarding a coil-specific examination position to the control unit for automatically moving the patient couch according to the coil-specific examination position.

15. The magnetic resonance device as claimed in claim 14, wherein the first input panel comprises a primary input panel or a secondary input panel arranged on the coil unit, the first input panel configured for signal transmission to the control unit upon activation, the signal transmission including the coil-specific examination position.

16. The magnetic resonance device as claimed in claim 14, wherein the coil unit has an optically detectable coil-specific marker, the device further comprising a detector for identifying the marker.

17. The magnetic resonance device as claimed in claim 16, wherein the marker and the detector system are arranged such that the marker is identified when the marker passes the detector.

18. The magnetic resonance device as claimed in claim 17, wherein the detector is arranged at an entrance to a patient accommodation area of the magnetic resonance device and at a level above the patient couch.

19. A coil unit for a magnetic resonance device, the coil unit configured to be arranged on a patient under magnetic resonance examination, the coil unit comprising an input panel configured to transmit upon activation a signal regarding a coil-specific examination position to the control unit for automatically moving the patient couch according to the coil-specific examination position.

20. The coil unit as claimed in claim 19, further comprising an optically detectable coil-specific marker.

* * * * *